US00PP33503P3

(12) United States Plant Patent
van Geest

(10) Patent No.: US PP33,503 P3
(45) Date of Patent: Sep. 21, 2021

(54) ***ALOCASIA* PLANT NAMED 'ESPE1904'**

(50) Latin Name: *Alocasia zebrina*
Varietal Denomination: ESPE1904

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 17/094,887

(22) Filed: Nov. 11, 2020

(65) Prior Publication Data

US 2021/0161054 P1 May 27, 2021

(51) Int. Cl.

| | |
|---|---|
| ***A01H 5/12*** | (2018.01) |
| ***A01H 6/00*** | (2018.01) |
| ***A01H 6/12*** | (2018.01) |

(52) U.S. Cl.
USPC ..... Plt./373
CPC ..... *A01H 6/12* (2018.05)

(58) Field of Classification Search
USPC ..... Plt./373
See application file for complete search history.

(56) References Cited

PUBLICATIONS

PLUTO Plant Variety Database May 11, 2021. p. 1.*

* cited by examiner

*Primary Examiner* — Annette H Para
(74) *Attorney, Agent, or Firm* — Samuel R. McCoy, Jr.

(57) ABSTRACT

'ESPE1904' is a distinctive *Alocasia* plant which is characterized by the combination of a compact growth habit, a relatively small dark green lamina borne on long prominently striped petioles, and the stability of all characteristics from generation to generation.

3 Drawing Sheets

Latin name of the genus and species: The Latin name of the genus and species of the novel variety disclosed herein is *Alocasia zebrina.*

Variety denomination: The inventive variety of *Alocasia* disclosed herein has been given the variety denomination 'ESPE1904'.

CROSS REFERENCE TO RELATED APPLICATIONS

This application claims priority to the Community Plant Variety Rights application number 2019/3119, filed Nov. 27, 2019 which is herein incorporated by reference.

BACKGROUND OF THE INVENTION

Parentage: 'ESPE1904' originated as a naturally occurring, whole-plant mutation of an unnamed *Alocasia zebrina* plant (not patented). In the summer of 2016, the inventor discovered the mutation at his commercial greenhouse in 's-Gavenzande, The Netherlands, growing amongst a cultivated population of unnamed *Alocasia zebrina* plants. The mutation was noted for its compact, densely-foliage habit and uniquely colored petioles and was subsequently isolated for further evaluation in order to confirm the distinctness and stability of the characteristics first observed. Upon confirmation of distinctness and stability, 'ESPE1904' was selected for commercialization in the spring of 2017.

Asexual Reproduction: Asexual reproduction of 'ESFIBE1801', by way of meristematic tissue culture, was first initiated in May of 2018 at a commercial greenhouse in 's-Gavenzande, The Netherlands. Through five subsequent generations, the unique features of this cultivar have proven to be stable and true to type.

SUMMARY OF THE INVENTION

The cultivar 'ESPE1904' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ESPE1904'. These characteristics in combination distinguish 'ESPE1904' as a new and distinct *Alocasia* cultivar:

1. *Alocasia* 'ESPE1904' exhibits a compact, densely-foliage growth habit; and
2. *Alocasia* 'ESPE1904' exhibits a relatively small, dark green lamina borne on a long petiole; and
3. *Alocasia* 'ESPE1904' exhibits a petiole with a very light brown general coloration, suffused with light yellow-green distally, with prominent black irregular axial stripes and blotches.

BOTANICAL DESCRIPTION OF THE PLANT

Figure 1:
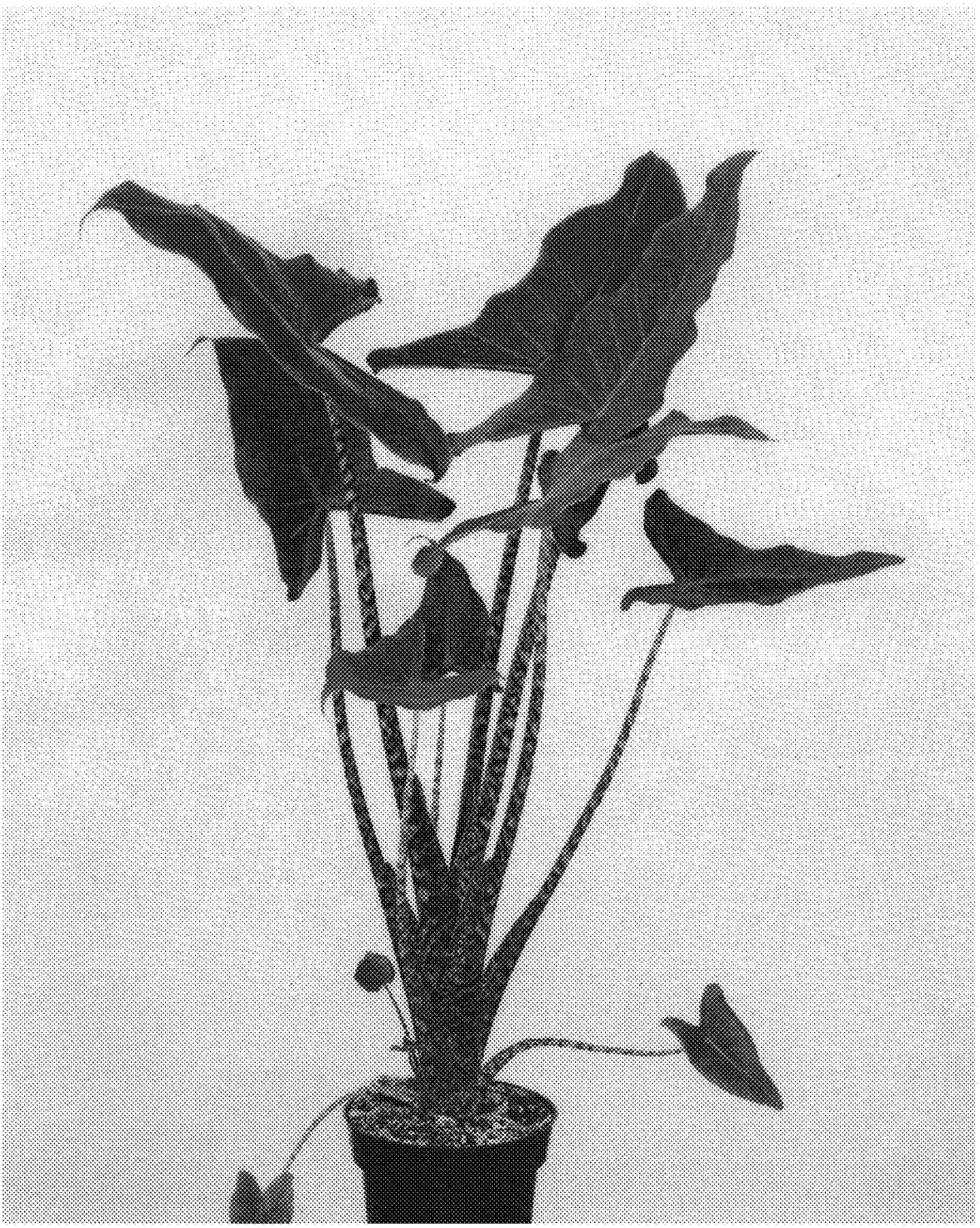
FIG. 1 illustrates, as nearly true as it is reasonably possible to make the same in color photographs of this type, two exemplary plants of 'ESPE1904' grown in a commercial greenhouse in Gavenzande, the Netherlands. These plants are approximately 9 months old, shown planted in a 12 cm container.
Figure 2:
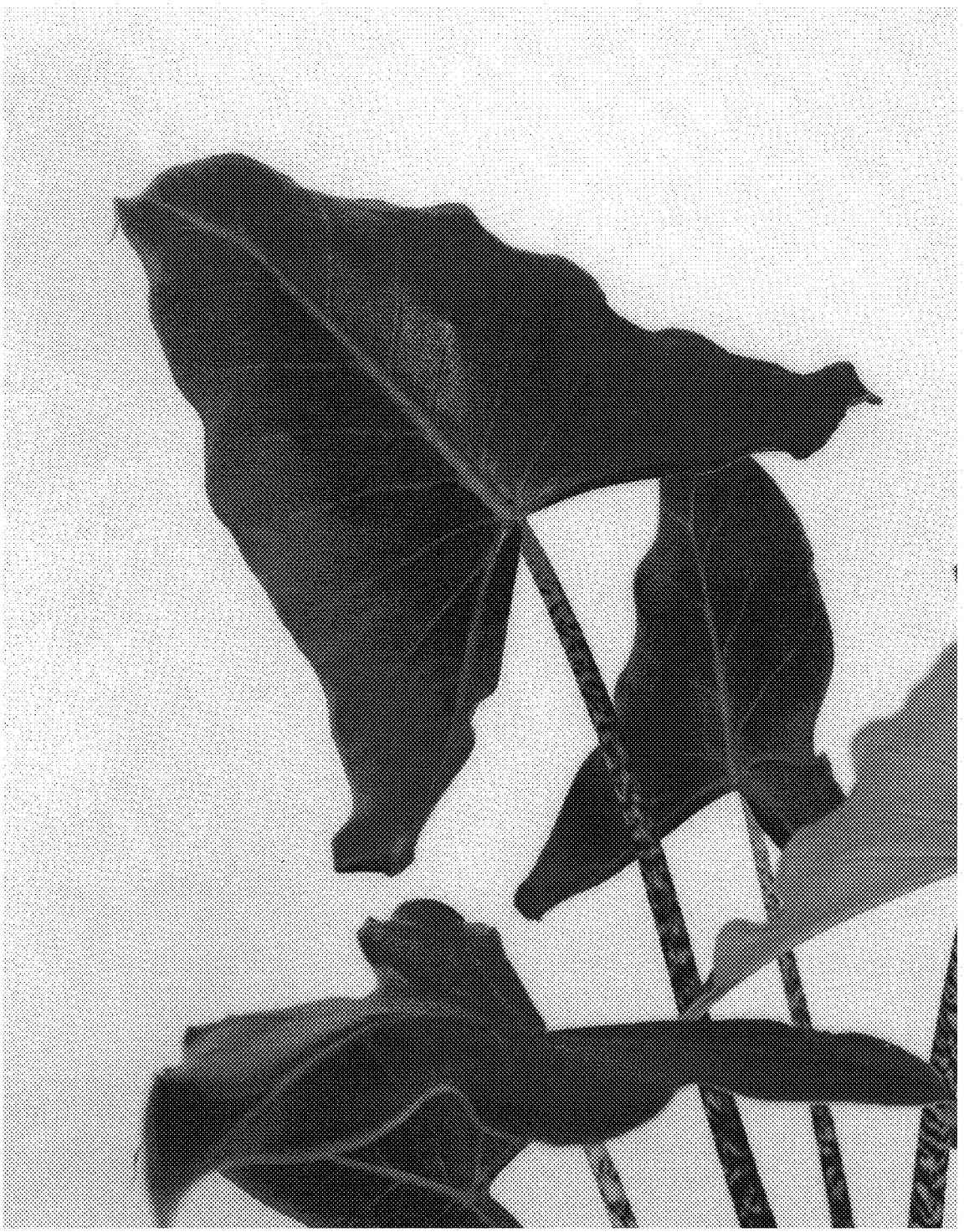
FIG. 2 illustrates, as nearly true as it is reasonably possible to make the same in color photographs of this type, the typical mature foliage of 'ESPE1904'.
Figure 3:
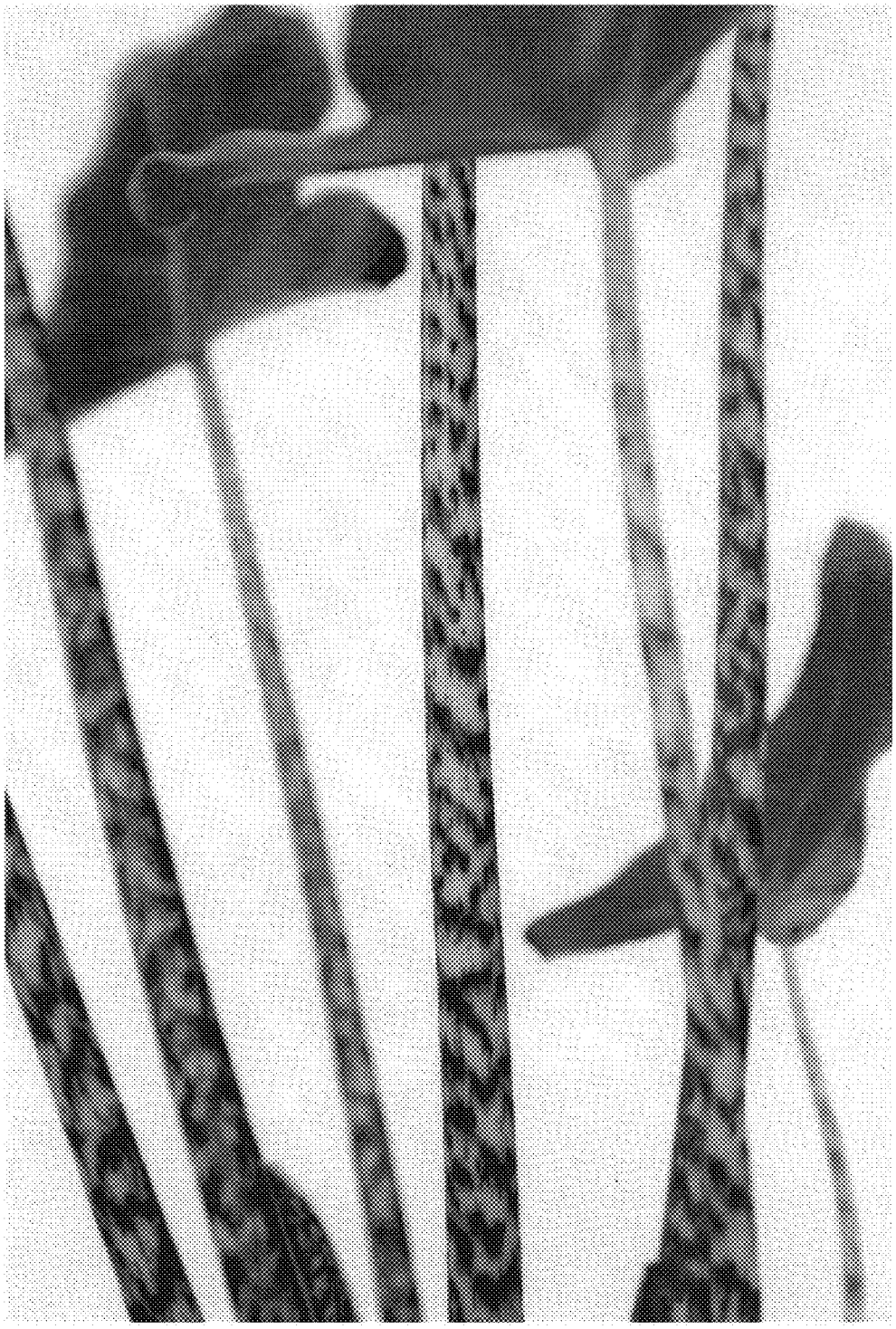
FIG. 3 illustrates, as nearly true as it is reasonably possible to make the same in color photographs of this type, the typical petiole of 'ESPE1904'.

The following observations and measurements made in August of 2020 describe averages from two 9 month-old 'ESPE1904' plants grown in a 12 cm nursery container at a greenhouse in 's-Gavenzande, the Netherlands. Plants were produced in a greenhouse with 50 percent shade covering, ebb and flood irrigation tables, no supplemental fertilizer, and no preventative or pest control measures utilized.

Those skilled in the art will appreciate that certain characteristics will vary with older or, conversely, with younger plants. 'ESPE1904' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'ESPE1904' and a comparison with the parent plant and most similar commercial comparator are provided below.

Plant description:

*Growth habit*.—Herbaceous perennial with a broad, upright growth habit; leaves growing from a basal clump.

*Plant shape*.—Broad obovate.

*Height from soil level to top of foliar plane*.—60.0 cm.

*Plant spread*.—50.5 cm.

*Growth rate*.—Fast.

*Plant vigor*.—Very vigorous.

*Propagation type*.—Stem cuttings.

*Time to produce a rooted cutting*.—Approximately 42 days to produce a rooted cutting at approximately 25 degrees Celsius.

*Time to produce a finished plant*.—Approximately 18 weeks to produce a marketable finished plant in a 17 cm pot.

*Disease and pest resistance or susceptibility*.—Neither susceptibility nor resistance to pests and diseases common to either *Alocasia* have been observed.

*Environmental tolerances*.—Adapt to temperatures as low as 5 degrees Celsius and as high as 40 degrees Celsius; moderate to high tolerance to rain; low tolerance to wind.

Roots:

*General*.—Moderately dense, moderately branched rooting; roots are fleshy.

*Distribution in the soil profile*.—Shallow to moderately deep.

*Diameter of roots*.—5.0 mm on average.

*Texture*.—Smooth; no root hairs.

*Color*.—White, nearest to RHS 155C.

Foliage:

*Quantity*.—10 leaves per clump; 1 clump as observed.

*Arrangement*.—Alternate.

*Attachment*.—Petiolate.

*Division*.—Simple.

*Lamina*.—Attitude — Ranging from near horizontal to slightly pendulous. Shape — Broad sagitate. Length — 23.7 cm, excluding the petiole. Width — 20.4 cm. Apex — Apiculate to aristate. Base — Sagitate; lobes free. Aspect — Flat to very slightly concave; curled downward at the apex in an average angle of 90 degrees to the balance of the lamina and axially twisted to approximately 30 degrees. Margins — Repand; moderately undulate. Texture and luster, adaxial surface — Coriaceous, glabrous; slightly to moderately glossy. Texture and luster, abaxial surface — Coriaceous, glabrous; slightly to moderately glossy. Color — Juvenile foliage, adaxial surface — Green, nearest to in between RHS 141A and 143A yet slightly darker. Juvenile foliage, abaxial surface — Nearest to in between yellow-green and greyed-green, nearest to RHS 1478 and 191A. Mature foliage, adaxial surface — Green, nearest to in between RHS NN137A and 139A. Mature foliage, abaxial surface — Yellow-green, nearest to RHS 146B. Venation — Pattern — Pinnate. Color, adaxial surfaces — Green, nearest to RHS NN137C. Color, abaxial surface — Nearest to in between yellow-green and greyed-green; RHS 147D, 148D, and 193A.

*Petiole*.—Attitude — Upright and slightly outward. Strength — Very strong. Length — 45.9 cm. Diameter — 1.7 cm, proximally, and 0.6 cm distally. Texture and luster, adaxial surface — Smooth, glabrous and matte. Texture and luster, abaxial surface — Smooth, glabrous and very strong. Color, adaxial surface — Yellow-green, nearest to RHS 152D, and lightly suffused with a darker shade of yellow-green distally, nearest to RHS 146D; prominent irregular axial stripes and blotches colored black, nearest to a mixture of RHS 203A and 203B. Color, abaxial surface — Yellow-green, nearest to RHS 152D, and lightly suffused with a darker shade of yellow-green distally, nearest to RHS 146D; prominent irregular axial stripes and blotches colored black, nearest to a mixture of RHS 203A and 203B. Sheath — Shape — Deltoid. Length — 16.7 cm. Width — 1.5 cm. Margin — Entire; not undulated. Texture and luster — Smooth, glabrous and glossy. Color, inner surface — Greyed-green, nearest to RHS 195B; prominent irregular axial stripes and blotches colored nearest to in between greyed-green and black, RHS N189A and 203A. Color, outer surface — Yellow-green, nearest to RHS 146D; prominent irregular axial stripes and blotches colored nearest to in between greyed-green and black, RHS N189A and 203A.

Inflorescence: To date, 'ESPE1904' has not flowered.

COMPARISONS WITH THE PARENT PLANTS

Plants of the new cultivar 'ESPE1904' differ from the parent, an unnamed *Alocasia zebrina* plant (not patented), in the characteristics described in Table 1 below.

TABLE 1

| Characteristic | 'ESPE1904' | The parent |
|---|---|---|
| Growth habit. | More compact than the parent. | Less compact than 'ESPE1904'. |
| Abundance of foliage. | More abundant. | Less abundant. |
| Foliage size. | Smaller than the parent. | Larger than 'ESPE1904'. |
| Prominence of the color pattern on the petioles. | More prominent. | Less prominent. |

COMPARISONS WITH THE CLOSEST KNOWN COMPARATOR

Plants of the new cultivar 'ESPE1904' differ from the closest known commercial comparator, *Alocasia zebrina* 'AARALZE001' (2017/0836), in the following characteristics described in Table 2 below.

TABLE 2

| Characteristic | 'ESPE1904' | 'AARALZE001' |
|---|---|---|
| Growth habit. | Less compact than 'AARALZE001'; suited to production in 12 cm nursery containers. | More compact than 'ESPE1904'; suited to production in 8.5 cm nursery containers. |
| Abundance of foliage. | More abundant. | Less abundant. |
| Foliage size. | Smaller than 'AARALZE001'. | Larger than 'ESPE1904'. |
| Size of the lamina. | Larger than 'AARALZE001'. | Smaller than 'ESPE1904'. |
| Petiole length. | Significantly longer than 'AARALZE001'. | Significantly shorter than 'ESPE1904'. |

That which is claimed is:

1. A new and distinct variety of *Alocasia* plant named 'ESPE1904', substantially as described and illustrated herein.

* * * * *